United States Patent
Tian

(10) Patent No.: US 9,193,910 B1
(45) Date of Patent: Nov. 24, 2015

(54) LIQUID CRYSTAL COMPOUND, LIQUID CRYSTAL COMPOSITION AND METHODS FOR PREPARING THE SAME, LIQUID CRYSTAL DISPLAY PANEL

(71) Applicant: BOE TECHNOLOGY GROUP CO., LTD., Beijing (CN)

(72) Inventor: Xiaoxiong Tian, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 14/600,384

(22) Filed: Jan. 20, 2015

(30) Foreign Application Priority Data

May 29, 2014 (CN) .......................... 2014 1 0236013

(51) Int. Cl.
  *C09K 19/48* (2006.01)
  *C09K 19/32* (2006.01)
  *C07C 1/30* (2006.01)
  *C07C 1/20* (2006.01)

(52) U.S. Cl.
  CPC . *C09K 19/32* (2013.01); *C07C 1/20* (2013.01); *C07C 1/30* (2013.01)

(58) Field of Classification Search
  CPC .......... C09K 19/32; C09K 19/48; C07C 1/20; C07C 1/30
  USPC ............... 252/299.01, 299.6, 299.61, 299.62, 252/299.63; 349/182; 428/1.1, 1.3; 585/25, 585/26

See application file for complete search history.

(56) References Cited

U.S. PATENT DOCUMENTS

| | | | | |
|---|---|---|---|---|
| 7,790,057 B2 * | 9/2010 | Busing | .................. | C07C 17/269 252/301.16 |
| 8,581,262 B2 * | 11/2013 | Pan | ........................ | B82Y 10/00 257/40 |
| 8,986,852 B2 * | 3/2015 | Stoessel | .................. | C07C 15/28 257/40 |

* cited by examiner

*Primary Examiner* — Geraldina Visconti
(74) *Attorney, Agent, or Firm* — Nath Goldberg & Meyer; Joshua B. Goldberg

(57) ABSTRACT

The present invention relates to the technical field of liquid crystal and discloses a liquid crystal compound and a method for producing the same, a liquid crystal composition and a method for producing the same, and a liquid crystal display panel. The structure of the liquid crystal compound is represented by the following formula. Since the liquid crystal compound has a higher clearing point and exhibits excellent physical and chemical stability, the liquid composition formed from the liquid crystal compound has a higher clearing point. When such a composition is used for preparing a liquid crystal layer, the crystal display panel comprising the liquid crystal layer can exhibit excellent displaying performances and thus can be used for various application fields.

P1

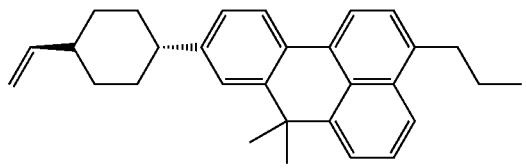

7 Claims, 1 Drawing Sheet

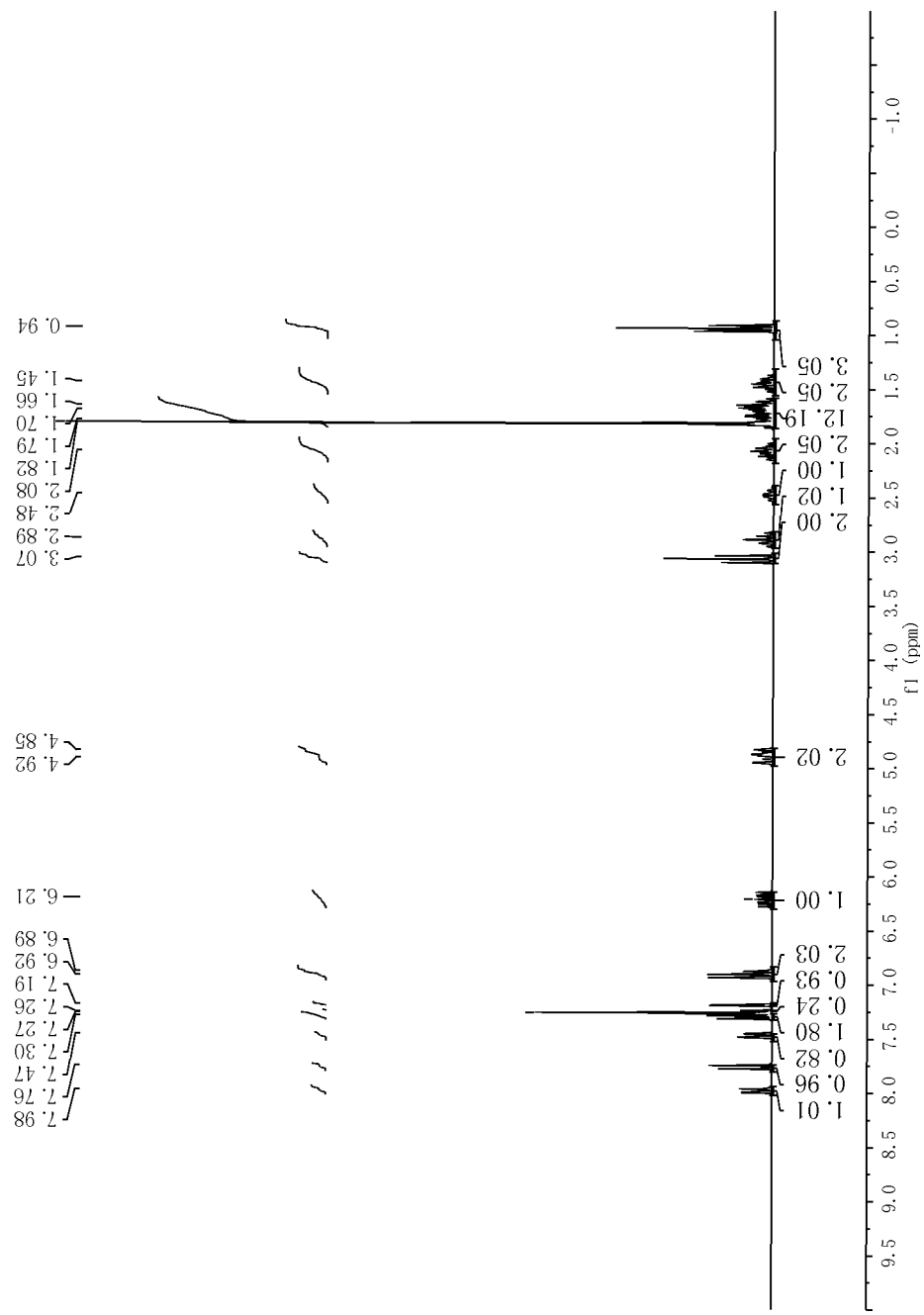

LIQUID CRYSTAL COMPOUND, LIQUID CRYSTAL COMPOSITION AND METHODS FOR PREPARING THE SAME, LIQUID CRYSTAL DISPLAY PANEL

FIELD OF THE INVENTION

The present invention relates to the technical field of liquid crystal (LC), particularly to an LC compound and a method for producing the same, an LC composition and a method for producing the same, and an LC display panel.

BACKGROUND OF THE INVENTION

The thin film transistor liquid crystal display (TFT-LCD) is dominantly used in a flat panel display device due to its various advantages, such as small volume, low power consumption, comparatively lower manufacture cost, free of radiation, etc.

LC displays have been widely used for various applications in the life. With the development of the LC display techniques, a variety of LC compounds have been used in practical applications. The properties of an LC compound concerned in these applications include phase transition temperature, optical anisotropy, dielectric anisotropy, viscosity, specific resistance of the LC compound. It is important in the art to develop a novel LC compound and a composition comprising the LC compound, so as to improve the properties thereof and further improve the application performances of the LC display.

The clearing point of the existing LC material is typically about 100° C., which is relatively low such that the application range of the LC display is limited.

SUMMARY OF THE INVENTION

The present invention provides an LC compound and the method for producing the same, an LC composition and the method for producing the same, and an LC display panel, so as to improve the clearing point of the LC compound, in turn broadening the application range of the LC display panel.

One aspect of the present invention relates to an LC compound P1 represented by the following formula.

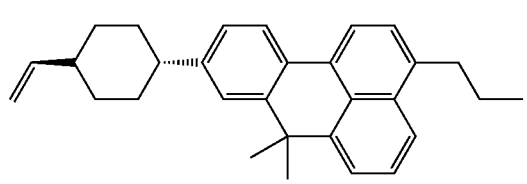

P1

Another aspect of the present invention relates to a method for producing the LC compound P1, including the following steps:

Step a: Performing a bromination reaction of Compound P1-1, so as to obtain Compound P1-2, as shown below:

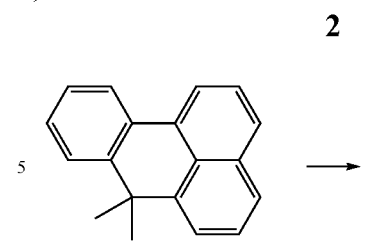

P1-1

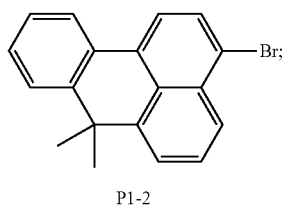

P1-2

Step b: Reacting Compound P1-2 with propyl magnesium bromide, so as to produce Compound P1-3, as shown below:

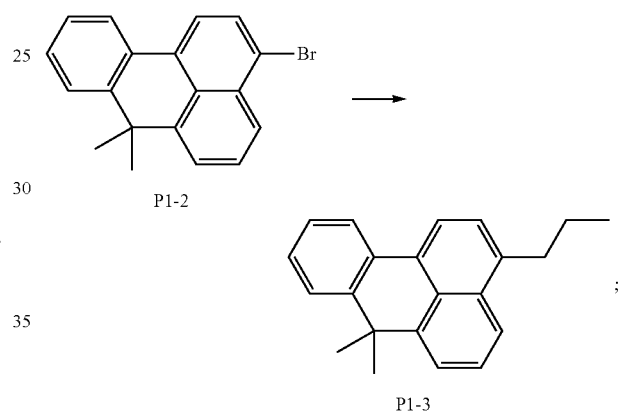

P1-2

P1-3

Step c: Performing a bromination reaction of Compound P1-3, so as to obtain Compound P1-4, as shown below:

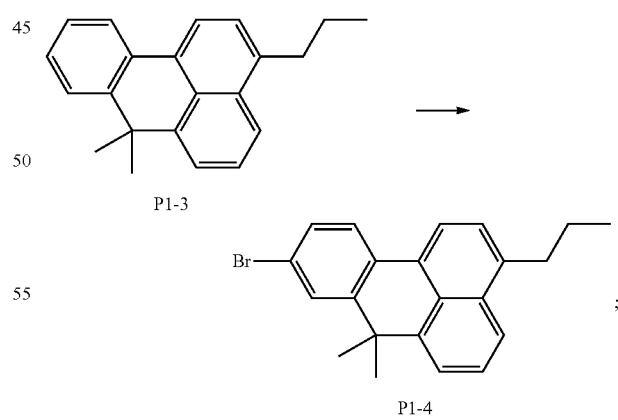

P1-3

P1-4

Step d: Producing a Grignard agent of Compound P1-4, and then performing an addition reaction of the Grignard agent of Compound P1-4 with

so as to produce Compound P1-5, as shown below:

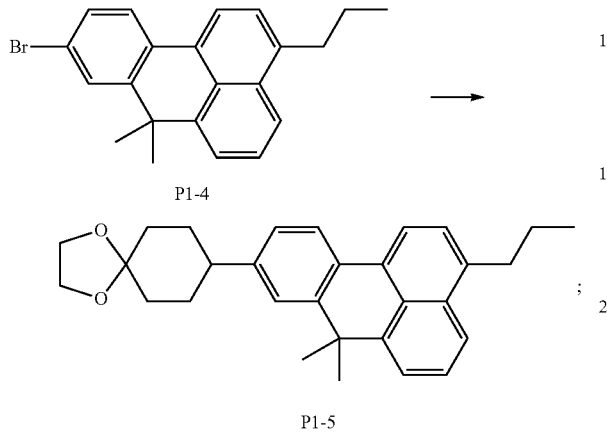

Step e: Performing a hydrolysis reaction of Compound P1-5, so as to produce Compound P1-6, as shown below:

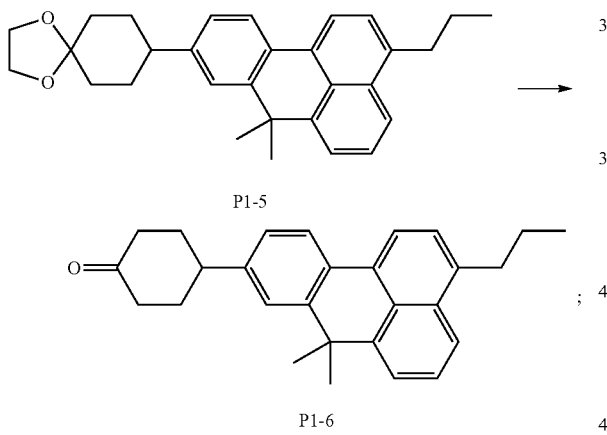

Step f: Performing a Witting reaction of Compound P1-6, followed with a hydrolysis reaction, so as to produce Compound P1-7, as shown below:

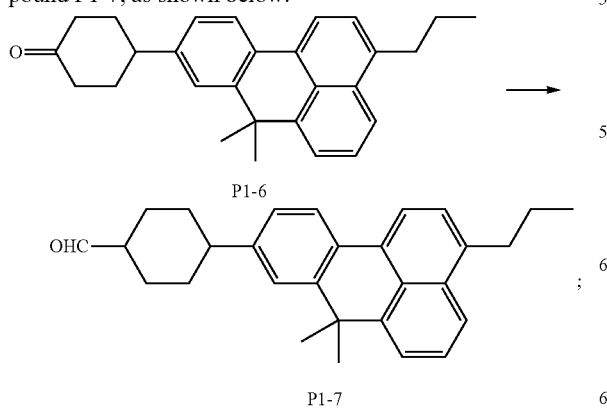

Step g: Performing a Witting reaction of Compound P1-7, so as to produce the Compound P1, as shown below:

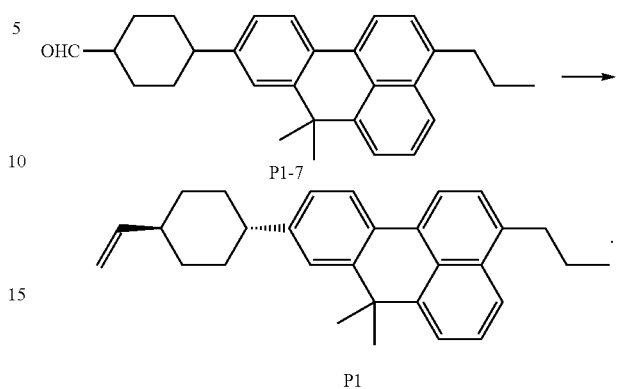

Another aspect of the present invention relates to an LC composition comprising the LC compound P1 as described above. Preferably, based on 100 mass % of the LC composition, the LC composition comprises 8-40 mass % of the LC compound P1.

Another aspect of the present invention relates to a method for preparing the LC composition as described above, comprising a step of mixing the components intended to be included in the composition.

The present invention further relates to an LC display panel comprising an LC layer produced by using the LC composition of the present invention.

BRIEF DESCRIPTION OF THE DRAWINGS

FIG. 1 is a $^1$H NMR spectrogram of Compound P1.

DETAILED DESCRIPTION OF CERTAIN EMBODIMENTS

In one embodiment of the present invention, a LC compound P1 represented by the following formula is provided,

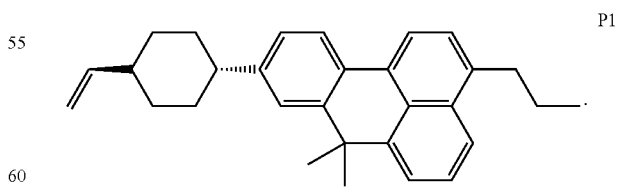

In one embodiment of the present invention, a method for producing the LC compound P1 as described above is provided, which comprises the following steps:

Step a: Performing a bromination reaction of Compound P1-1, so as to obtain Compound P1-2, as shown below:

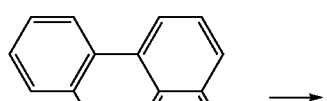

P1-1

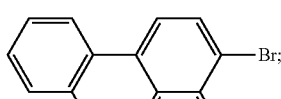

P1-2

Step b: Reacting Compound P1-2 with propyl magnesium bromide, so as to produce Compound P1-3, as shown below:

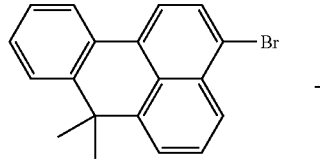

P1-3

Step c: Performing a bromination reaction of Compound P1-3, so as to obtain Compound P1-4, as shown below:

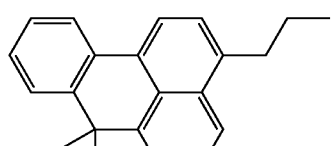

P1-4

Step d: Producing a Grignard agent of Compound P1-4, and then performing an addition reaction of the Grignard agent of Compound P1-4 with

so as to produce Compound P1-5, as shown below:

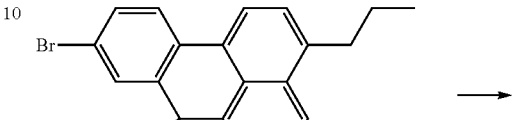

P1-4

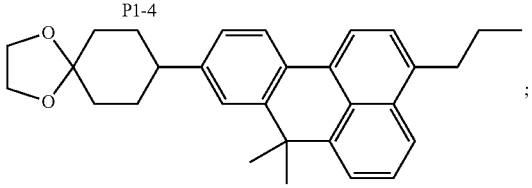

P1-5

Step e: Performing a hydrolysis reaction of Compound P1-5, so as to produce Compound P1-6, as shown below:

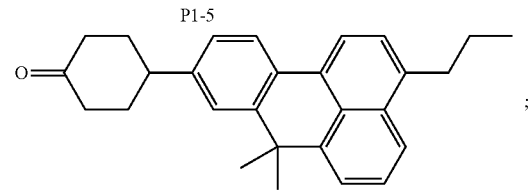

P1-5

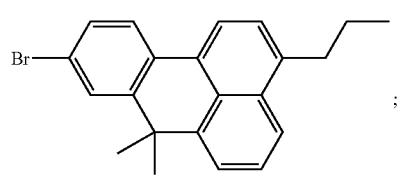

P1-6

Step f: Performing a Witting reaction of Compound P1-6, followed by a hydrolysis reaction, so as to produce Compound P1-7, as shown below:

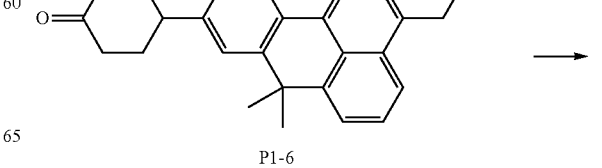

P1-6

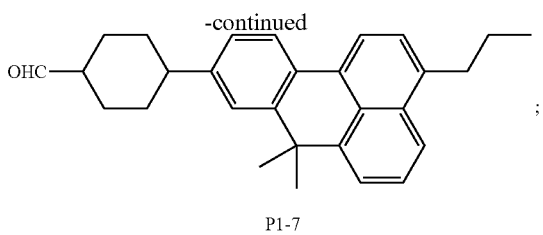

P1-7

Step g: Performing a Witting reaction of Compound P1-7, so as to produce the Compound P1, as shown below:

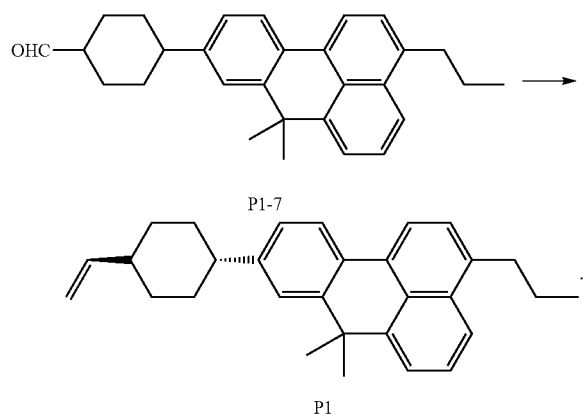

In one embodiment, in the Step a, Compound P1-1 may be reacted with N-bromobutanimide (NBS). In one embodiment, the solvent used in the bromination reaction may be tetrahydrofuran (THF).

In one embodiment, in the Step b, Compound P1-2 may be reacted with propyl magnesium bromide. In one embodiment, the solvent used in this reaction may be toluene. When Compound P1-2 is reacted with propyl magnesium bromide, the molar ratio of Compound P1-2 to propyl magnesium bromide is in the range of 1:1.5-1:4, and the reaction temperature may be increased gradually from 20° C. to 60° C.

In one embodiment, in the Step c, Compound P1-3 may be reacted with Br$_2$, so as to produce Compound P1-4. In one embodiment, the solvent used in this reaction may be methylene chloride. Compound P1-4 may be separated from the mixture obtained from the reaction.

In one embodiment, when Compound P1-3 is reacted with Br$_2$, the molar ratio of Compound P1-3 to Br$_2$ is in the range of 1:1-1:1.5, and the reaction temperature may be increased from 17° C. to 33° C.

In one embodiment, after the addition reaction, the resulted product is subject to a dehydration reaction, followed by a reduction reaction, thereby obtaining Compound P1-5.

In one embodiment, in the step d, the molar ratio of Compound P1-4 to

is in the range of 1:1-1:1.8.

In one embodiment, in the step e, the hydrolysis reaction is carried out in the presence of formic acid, and the solvent used in the hydrolysis reaction may be toluene. In one embodiment, in the step e, the molar ratio of Compound P1-5 to the formic acid is in the range of 1:1.5-1:5, and the reaction temperature may be increased from 55° C. to 132° C.

In one embodiment, the Witting reaction is carried out in the presence of a methoxymethyl phosphinium chloride and a potassium t-butoxide.

In one embodiment, in the step f, the molar ratio of Compound P1-6 to the methoxymethyl phosphinium chloride is in the range of 1:1-1:1.2, the reaction temperature may be increased from −20° C. to 35° C., and the reaction time may be in the range of 30-60 mins. In one embodiment, the hydrolysis reaction is carried out in the presence of hydrochloric acid.

In one embodiment, in the Step g, the witting reaction is carried out in the presence of a methyl phosphinium bromide and a potassium t-butoxide.

In one embodiment, in the Step g, the molar ratio of Compound P1-7 to the methyl phosphinium bromide is in the range of 1:1-1:1.2, and the reaction temperature may be increased gradually from −20° C. to 35° C.

In a preferred embodiment, the LC compound P1 is prepared by a method comprising Steps a-g as below.

Step a

Compound P1-1 is reacted with NBS in THF so as to produce Compound P1-2, as shown below, wherein Compound P1-2 is obtained upon separating from the reaction mixture.

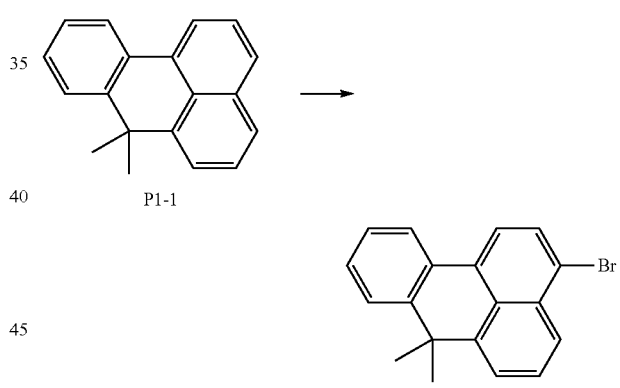

Step b

Compound P1-2 is reacted with propyl magnesium bromide in methylene chloride, so as to produce Compound P1-3, as shown below, wherein Compound P1-3 is obtained upon separating from the reaction mixture.

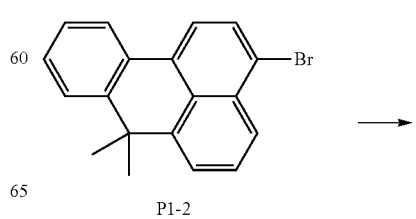

P1-2

-continued

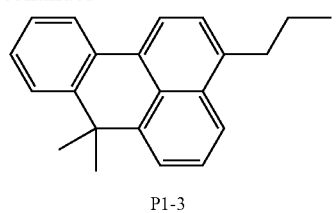

P1-3

Step c

Compound P1-3 is reacted with Br$_2$, so as to obtain Compound P1-4, as shown below, wherein Compound P1-4 is obtained upon separating from the reaction mixture.

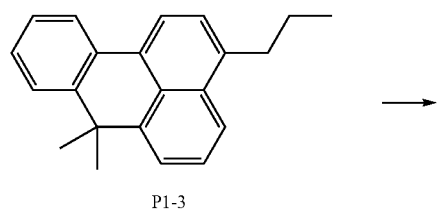

P1-4

Step d

A Grignard agent of Compound P1-4 is produced, and then the Grignard agent of Compound P1-4 is reacted with

followed by a dehydration reaction and a reduction reaction, so as to produce Compound P1-5, as shown below.

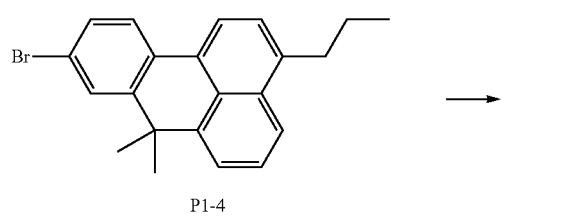

P1-5

Step e

Compound P1-5 is reacted with formic acid in toluene through a hydrolysis reaction, so as to produce Compound P1-6, as shown below.

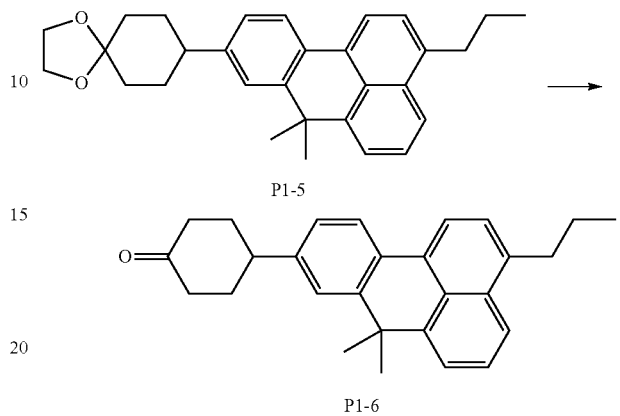

Step f

Compound P1-6 is reacted with methoxymethyl triphenylphosphinium chloride in the presence of potassium t-butoxide through a Witting reaction, followed by a hydrolysis reaction in the presence of hydrochloric acid, so as to produce Compound P1-7, as shown below.

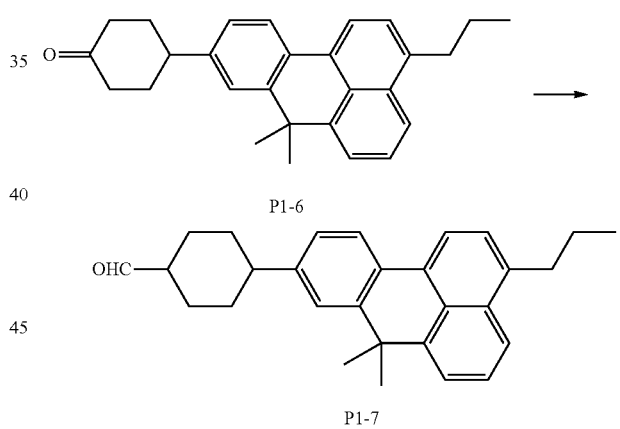

Step g

Compound P1-7 is reacted with methyl triphenylphosphinium bromide in the presence of potassium t-butoxide through a Witting reaction, so as to produce Compound P1, as shown below, wherein Compound P1 is obtained upon separated from the reaction mixture.

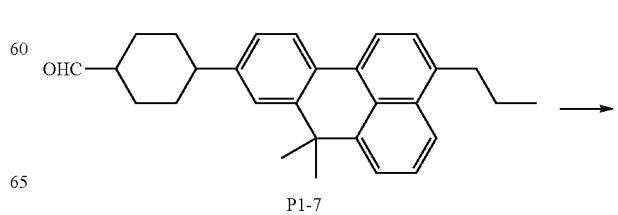

P1-7

-continued

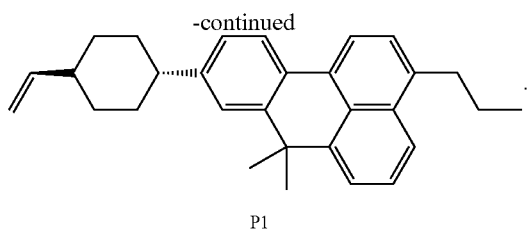

P1

The LC composition of the present invention comprises 8-40 mass % of the LC compound P1 as described above.

In a preferred embodiment of the present invention, the LC composition comprises:

3-15 mass % of Compound A:

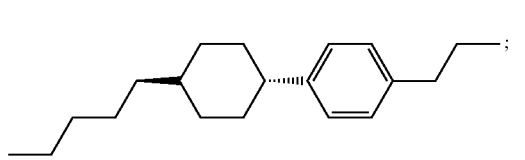

A 8-20 mass % of Compound B

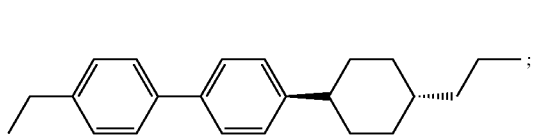

B 10-25 mass % of Compound C:

C 8-20 mass % of Compound D:

D 8-30 mass % of Compound E:

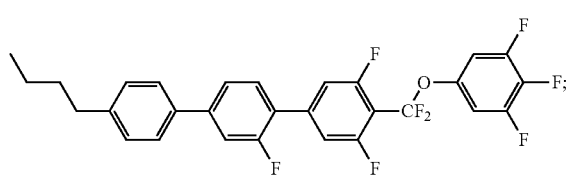

E 10-20 mass % of Compound F:

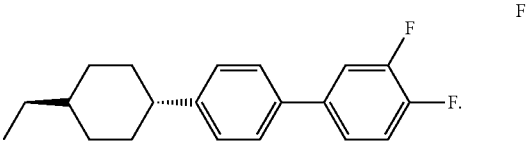

F

In a more preferred embodiment of the present invention, the LC composition comprises: 6 mass % of Compound A, 15 mass % of Compound B, 15 mass % of Compound C, 13 mass % of Compound D, 12 mass % of Compound E, 17 mass % of Compound F, and 22 mass % of the LC compound P1.

The method for preparing the LC composition of the present invention comprises the step of mixing the components intended to be included in the composition.

The LC display panel of the present invention is characterized in that the LC layer of the LC display panel is produced by using the LC composition of the present invention.

The LC compound P1 of the present invention is a novel 7-hydrogen benzo[de]anthracene LC compound, which has a clearing point up to 292° C. and has good physical and chemical stability. The LC compound P1 can be incorporated into a composition such that the clearing point of the resulted composition is above 120° C., which is dramatically greater than the clearing points of the existing LC material. When the LC composition is used for an LC display panel, the application field of the LC display panel can be broadened greatly.

EXAMPLES

Next, in order to illustrate the objects, technical solutions and advantages of the present invention, the present invention will be described in detail with reference to below examples, which are not intended to limit the scope of the present invention. The LC compound and the method for producing the same, the LC composition and the method for producing the same, and the LC display panel of the present invention can be better understood with reference to these examples. The LC display panel of the present invention can be widely used for various applications.

The LC compound P1 of the present invention has a clearing point of up to 292° C. when the LC compound P1 is used for forming an LC composition, the clearing point of the resulted LC composition can be up to above 120° C., which is dramatically greater than the clearing points of the existing LC materials. If the LC composition is used for an LC display panel, the application field of the LC display panel can be greatly broadened.

The agents used in the examples of the present invention are commercially available. The nuclear magnetic resonance spectrometer used in the examples of the present invention is Bruker Avance III 500 (500 MHz), and the mass spectrometer used in the examples of the present invention is GCMS-QP2010SE obtained from SHIMADZU Corporation in Japan.

The LC compound P1 prepared in the example of the present invention is represented by the following formula

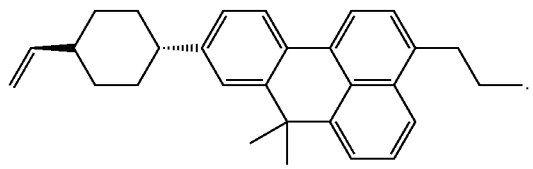

P1

Preparation Example 1

Preparation of the LC Compound P1

The Compound P1 is prepared as follows:

Step a

In a 250 mL three-necked flask, 2.5 g of 7,7-dimethyl-7H-benzo[de]anthracene (i.e. Compound P1-1, see WO2011/115378) was dissolved in 50 mL of THE Upon stirring, 1.8 g of NBS was added. The reaction mixture was heated to 35° C. and maintained under this temperature for 1 hr. Then 80 mL of water was added into the reaction mixture. A yellow solid was precipitated. The solid is filtered and dried. The obtained product (i.e. Compound P1-2) is detected by using GCMS-QP2010SE. The mass spectrum detection of the product gives a result of m/e: 324.

Step b

In a 250 mL three-necked flask, 2.9 g of Compound P1-2 obtained from Step a was dissolved in 50 mL of toluene. Then a catalytic amount of terakis(triphenylphosphine) palladium (0) as a catalyst was added. Upon stirring and under a temperature of 30° C., 27 g of 15% THF solution of propyl magnesium bromide was dropped into the flask. Subsequently, the reaction mixture was maintained under such a temperature for 3 hrs. Thereafter, water was added into the reaction mixture, and the organic layer therein was separated, washed with water, dried by magnesium sulfate, filtrated and purified through silica column chromatography (eluent: petroleum ether:methylene chloride=10:1). The obtained product (i.e. Compound P1-3) was detected by using GCMS-QP2010SE. The mass spectrum detection of the product gives a result of m/e: 286.

Step c

In a 250 mL three-necked flask, 2.55 g of Compound P1-3 obtained in Step b was dissolved into 50 mL of methylene chloride. The reaction temperature was controlled to be 25° C. 1.6 g $Br_2$ in 5 mL of methylene chloride was dropped into the flask. Thereafter, the reaction mixture was maintained under the temperature of 25° C. for 2 hrs. after the reaction was completed, water was added into the reaction mixture, and the organic layer therein was separated, washed with an aqueous solution of sodium hydrogen sulfite followed with water, dried by magnesium sulfate, filtrated and purified through silica column chromatography (eluent: petroleum ether:methylene chloride=10:1). The obtained product (i.e. Compound P1-4) was detected by using GCMS-QP2010SE. The mass spectrum detection of the product gives a result of m/e: 366.

Step d 0.28 g of magnesium, 5 mL of THF and a small amount of 1,2-dibromoethane were charged into a 250 mL three-necked flask. After the reaction was initiated, 3.5 g of Compound P1-4 in 20 mL THF solution was dropped into the flask upon stirring. Thereafter, the reaction mixture was refluxed for 30 mins so as to obtain a Grignard agent. Subsequently, the reaction mixture was cooled to 25° C. A solution formed from 1.8 g

and 10 mL THF was added. Thereafter, the obtained mixture was refluxed for 30 mins, and then cooled to room temperature. An aqueous solution of ammonium chloride was added so as to initiating a hydrolysis reaction. After the hydrolysis reaction was completed, the organic layer was separated and washed with water. 300 mL of toluene, 2 g of ethylene glycol and 2 g of p-toluene sulfonic acid monohydrate were added into the organic layer and the resulted mixture was refluxed, meanwhile, the produced water was removed by using a Dean-Stark trap for 15 hrs. The mixture was cooled, washed with water. The organic layer was separated and concentrated to dry. Then, the product obtained therefrom was transferred to an autoclave, and 20 mL of toluene, 20 mL of ethyl acetate and 0.3 g of 5% Pd/C were charged into the autoclave. The autoclave was purged with hydrogen gas. Subsequently, the hydrogenation reaction was initiated under 0.1 MPa and for 2 hrs. After the reaction was completed, the catalyst was removed from the reaction solution. Then the reaction solution was concentrated to dry. The obtained product was purified through silica column chromatography (eluent: petroleum ether:methylene chloride=10:1). The obtained product (i.e. Compound P1-5) was detected by using GCMS-QP2010SE. The mass spectrum detection of the product gives a result of m/e: 426.

Step e

In a 250 mL three-necked flask, 3.9 g of Compound P1-5 obtained in Step d was dissolved in 50 mL toluene. Upon stirring, 1.5 g of 80% formic acid aqueous solution was added into the flask. The reaction mixture was refluxed for 2 hrs. Thereafter, the mixture was cooled and washed with water. The organic layer was separated from the mixture and concentrated to dry. The obtained product was purified upon recrystallization in petroleum ether. The product (i.e. Compound P1-6) was detected by using GCMS-QP2010SE. The mass spectrum detection of the product gives a result of m/e: 382.

Step f 2.87 g of methoxymethyl triphenylphosphinium chloride and 20 mL of THF were charged into a 500 mL three-necked flask and cooled to −10° C. Then 0.95 g of potassium t-butoxide was added in batches into the flask. Then a solution formed by dissolving 3.2 g of Compound P1-6 obtained in Step e into 10 mL THF was dropped into the flask. The reaction temperature was gradually increased to 25° C. and maintained for 40 mins. Water was added into the obtained mixture. The organic layer was separated and concentrated to dry. The resulted product was mixed with 30 mL of petroleum ether into a round-bottom flask so as to obtain a mixture. Upon sufficiently stirring, a solid was precipitated from the mixture. The mixture was filtrated under vacuum so as to remove the solid. The resulted filtrate was concentrated to dry, subsequently mixed with 50 mL of methylene chloride and 10 mL of 35% hydrochloric acid and then refluxed for 30 mins. The obtained mixture was cooled and decanted. The obtained decantate was washed with water until it is neutral. Then the organic layer was separated and concentrated to dry. The resulted product was purified upon recrystallization in a mixture solvent of petroleum ether and ethanol. The product was (i.e. Compound P1-7) was detected by using GCMS-QP2010SE. The mass spectrum detection of the product gives a result of m/e: 396.

Step g 3.8 g of methyl triphenylphosphinium bromide and 20 mL of THF were charged into a 500 mL three-necked flask and cooled to −10° C. Then 1.35 g of potassium t-butoxide was added in batches into the flask. Then a solution formed by dissolving 3.9 g of Compound P1-7 obtained in Step f into 10 mL THF was dropped into the flask. The reaction temperature was gradually increased to 25° C. and maintained for 40 mins. Water was added into the obtained mixture. The organic layer was separated and concentrated to dry. The resulted product was mixed with 30 mL petroleum ether into a round-bottom flask so as to obtain a mixture. Upon sufficiently stirring, a solid was precipitated from the mixture. The mixture was filtrated under vacuum so as to remove the solid. The resulted filtrate was concentrated to dry so as to obtain a crude product. The crude product was purified upon recrystallization in a mixture solvent of petroleum ether and ethanol so as to remove the isomer in a cis-configuration. The product was detected by GCMS-QP2010SE and characterized by using Bruker Avance III 500 (500 MHz, CDCl$_3$). The mass spectrum detection of the product gives a result of m/e: 394. The $^1$H NMR spectrogram of the product is shown in FIG. 1. As shown in FIG. 1, the product has a structure of the formula below (i.e. Compound P1):

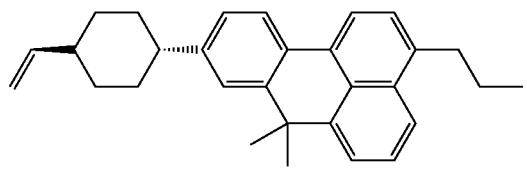

P1

7,7-dimethyl-3-propyl-9-((1 s,4s)-4-vinylcyclohexyl)-7H-benzo[de]anthracene

According to the spectrogram shown in FIG. 1, the peaks at the chemical shift (δ) of about 2.48 correspond to the H atom on 4-carbon of the cyclohexyl group, and the peak at δ2.89 corresponds to the H atom on 1-carbon of the cyclohexyl group. Such a spectrogram demonstrates that the cyclohexyl group is in trans-configuration.

Measurement of the Clearing Point of the LC Compound P1

The clearing point of the LC compound P1 was measured by using Differential Scanning calorimeter (DSC, TA-Q20, obtained from TA Instruments in USA).

The result shows that the clearing point of the LC compound P1 is 292° C. the clearing points of the following compounds were measured in the same manner as that of Compound P1.

Preparation Example 2

Preparation of an LC Composition

In this Example, the used components excluding the LC compound P1 were commercially available.

In particular, the LC compositions of this Example were prepared by mixing the components shown in the table 1 together.

LC Compositions 1-7

The mass fractions of each component are shown in Table 1. The LC compositions 1-7 were prepared by mixing these components. The clearing points of the LC compositions were shown in Table 1.

TABLE 1

The mass fractions of the components used for preparing the LC compositions and the clearing points thereof

| Fraction (mass %) | Com. A | Com. B | Com. C | Com. D | Com. E | Com. F | Com. P1 | Clearing point (° C.) |
|---|---|---|---|---|---|---|---|---|
| Composition 1 | 3 | 8 | 20 | 15 | 25 | 18 | 11 | 126 |
| Composition 2 | 6 | 15 | 15 | 13 | 12 | 17 | 22 | 133 |
| Composition. 3 | 12 | 10 | 10 | 8 | 30 | 15 | 15 | 127 |
| Composition. 4 | 15 | 18 | 25 | 12 | 12 | 10 | 8 | 129 |
| Composition. 5 | 10 | 20 | 15 | 12 | 8 | 16 | 19 | 131 |
| Composition. 6 | 8 | 12 | 18 | 20 | 12 | 20 | 10 | 130 |
| Composition. 7 | 5 | 15 | 12 | 8 | 10 | 10 | 40 | 132 |

(Note: Com. is an abbreviation of compound)

As shown in Table 1, the clearing points of the LC compositions are in the range of 126-133° C., thereby exhibiting good physical and chemical stability, so that the LC material produced from the LC composition can be used for more application fields with respect to the existing LC materials.

An LC layer was produced from any one of the LC compositions 1-7. And an LC display panel was manufactured from the LC layer. Thereby, the LC display panel exhibits excellent displaying performances and thus can be used for various application fields.

It should be understood that the above embodiments of the invention have been disclosed only for illustrating the principle of the present invention, but they are not intended to limit the present invention. Obviously, the person skilled in the art can make various modifications and variations of the invention without departing from the spirit and scope of the invention, thus the modifications and variations of the invention are included within the scope of the present invention.

The invention claimed is:

1. A liquid crystal compound P1 represented by the following formula

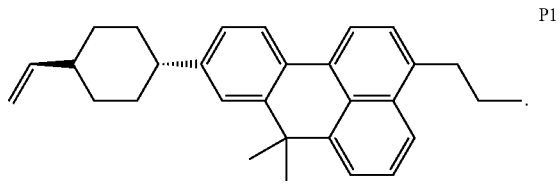

P1

2. A method for producing a liquid crystal compound P1 represented by the following formula

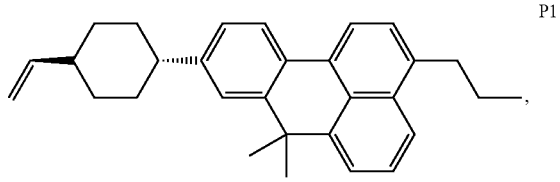

P1 wherein the method comprises the following steps:

Step a: Performing a bromination reaction of compound P1-1, so as to obtain Compound P1-2, as shown below:

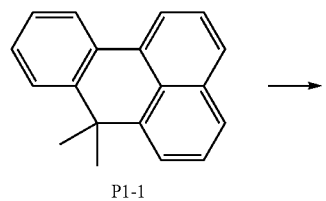

P1-1

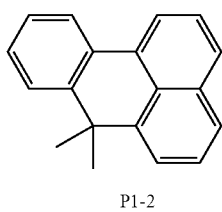

P1-2

Step b: Reacting the Compound P1-2 with propyl magnesium bromide, so as to produce Compound P1-3, as shown below:

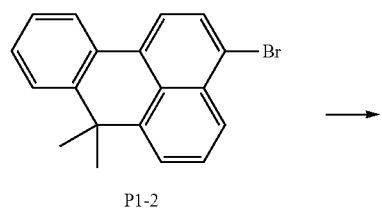

P1-2

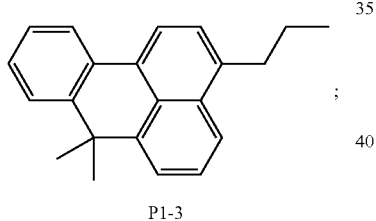

P1-3

Step c: Performing a bromination reaction of the Compound P1-3, so as to obtain Compound P1-4, as shown below:

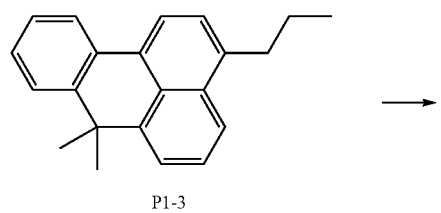

P1-3

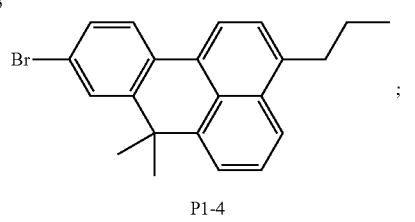

P1-4

Step d: Producing Grignard agent of Compound P1-4, and then performing an addition reaction of the Grignard agent of Compound P1-4 with

so as to produce Compound P1-5, as shown below:

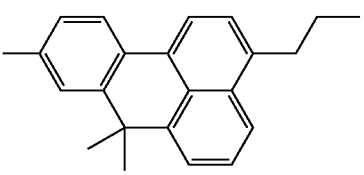

P1-4

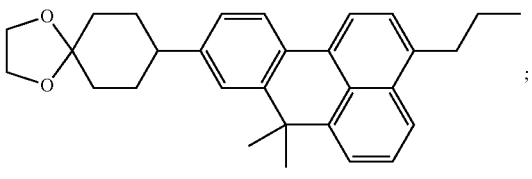

P1-5

Step e: Performing a hydrolysis reaction of Compound P1-5, so as to produce Compound P1-6, as shown below:

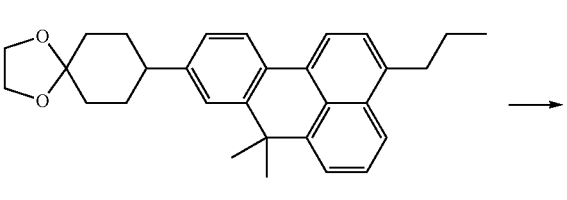

P1-5

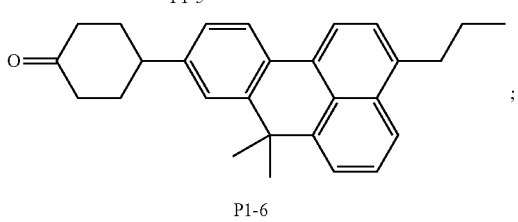

P1-6

Step f: Performing a Witting reaction of Compound P1-6, followed with a hydrolysis reaction, so as to produce Compound P1-7, as shown below:

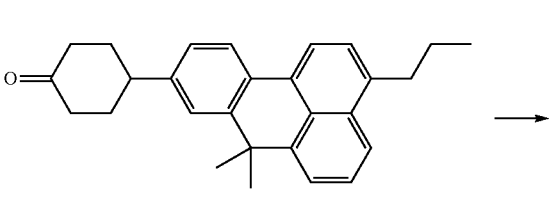

P1-6

-continued

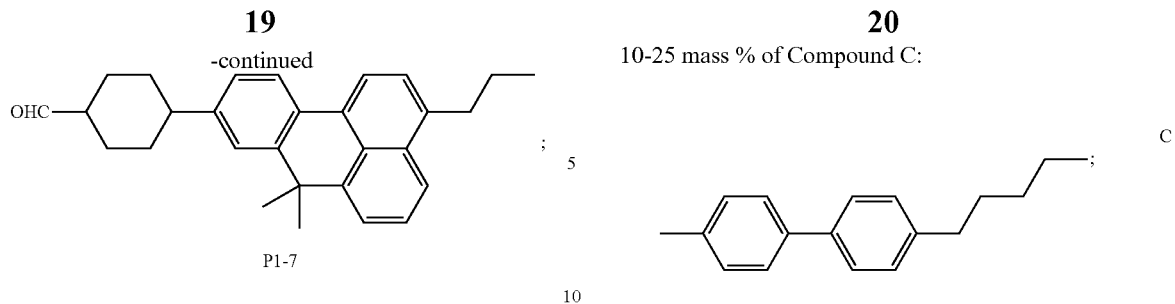

P1-7

Step g: Performing a Witting reaction of Compound P1-7, so as to produce Compound P1, as shown below:

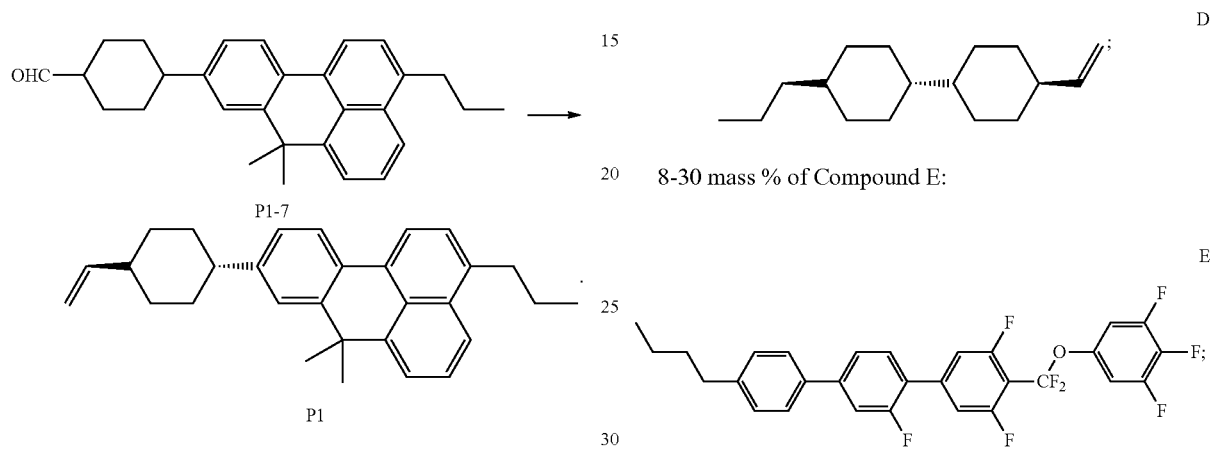

3. A liquid crystal composition, wherein, based on 100 mass % of the liquid crystal composition, the liquid crystal composition comprises 8-40 mass % of a liquid crystal compound P1 represented by the following formula

P1

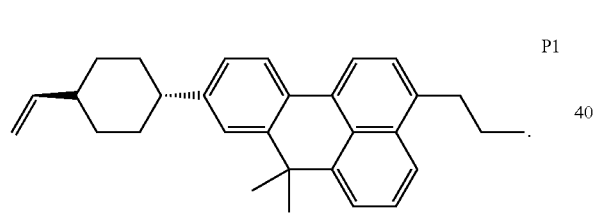

4. The liquid crystal composition of claim 3, further comprising the following components:
3-15 mass % of Compound A:

A

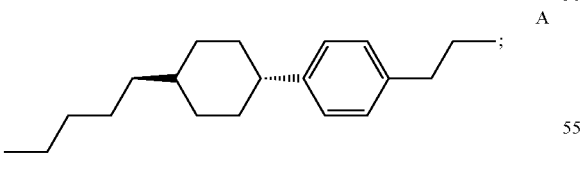

8-20 mass % of Compound B:

B

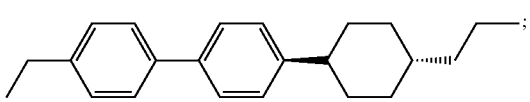

10-25 mass % of Compound C:

C 8-20 mass % of Compound D:

D 8-30 mass % of Compound E:

E 10-20 mass % of Compound F:

F

5. The liquid crystal composition of claim 4, comprising:
6 mass % of Compound A, 15 mass % of Compound B, 15 mass % of Compound C, 13 mass % of Compound D, 12 mass % of Compound E, 17 mass % of Compound F, and 22 mass % of Compound P1.

6. A method for preparing a liquid crystal composition, wherein the liquid crystal composition comprises 8-40 mass % of a liquid crystal compound as represent by the following formula, based on 100 mass % of the liquid crystal composition

P1

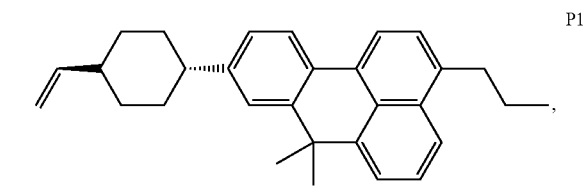

wherein the method comprises the step of mixing the components intended to be included in the liquid crystal composition.

7. A liquid crystal display panel comprising a liquid crystal layer, wherein the liquid crystal layer is produced by using a liquid crystal composition comprising 8-40 mass % of a liquid crystal compound as represent by the following formula, based on 100 mass % of the liquid crystal composition
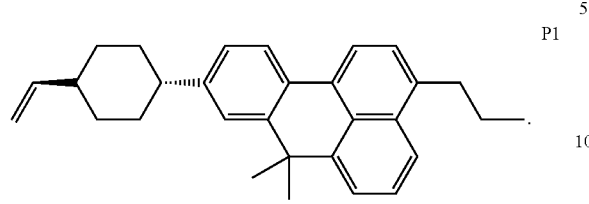
* * * * *